United States Patent [19]

Watanabe

[11] Patent Number: 5,019,081

[45] Date of Patent: May 28, 1991

[54] LAMINECTOMY SURGICAL PROCESS

[76] Inventor: Robert S. Watanabe, 11645 Wilshire Blvd., Suite 701, Los Angeles, Calif. 90025

[21] Appl. No.: 940,281

[22] Filed: Dec. 10, 1986

[51] Int. Cl.$^5$ ............................................. A61B 1/32
[52] U.S. Cl. ...................................... 606/79; 606/90; 606/105; 606/167; 606/184
[58] Field of Search .............. 128/92 Y, 92 Z, 92 R, 128/92 VZ, 92 V, 20, 330, 345, 92 ZZ, 92 VT, 329 R; 606/79, 83, 90, 105, 167, 171, 174, 175, 184, 185

[56] References Cited

U.S. PATENT DOCUMENTS 4,034,746 7/1977 Williams ............................ 128/345

FOREIGN PATENT DOCUMENTS 0787015 12/1980 U.S.S.R. ............................ 128/92 V

OTHER PUBLICATIONS

Clemente, 3rd Ed., '87, Urban & Schwarzeberg.
Zimmer Instruments, 1955.
V. Mueller & Co., Sep. 1963, Journal of Bone and Joint Surgery, vol. 45-A.

Primary Examiner—C. Fred Rosenbaum

[57] ABSTRACT

A microscopic lumber laminectomy surgical process and procedure which includes the steps of punching a hole in the supraspinous ligament, instead of removing the ligament, and of inserting a lamina spreader instrument through the hole and operating the spreader to open up the interspace between the lamina of the spinal column, with the ligament serving to stabilize the spine, and also serving to prevent the spreader from slipping out of the wound.

2 Claims, 3 Drawing Sheets

LAMINECTOMY SURGICAL PROCESS

BACKGROUND OF THE INVENTION

During microscopic lumbar laminectomy surgical procedures, it is usually necessary to open up the interspace between the lamina, so as to allow the surgical procedure to be performed with a minimum of bone excision. Lamina spreaders are known to the art, but the prior art surgical procedures require extensive dissection and complete removal of the supraspinous ligament in order to position the spreader, and the spreaders have a tendency to slip out of the wound.

In the practice of the process of the present invention an interspinous punch is used to punch a hole in the supraspinous ligament through which the spreader is inserted. Accordingly, the supraspinous ligament remains intact, and this serves to stabilize the spine. Moreover, since the spreader is inserted through the hole in the ligament, the ligament serves to hold the spreader in place and to prevent it from slipping out of the wound.

The lamina spreader serves to spread out the lamina and enables the surgeon to enter the interlaminal area with minimal removal of bone. The lamina spreader used in the process of the invention is curved to keep it out of the way of the microscope and of the surgeon during the surgical procedure.

DETAILED DESCRIPTION OF THE ILLUSTRATED EMBODIMENT

Figure 1:
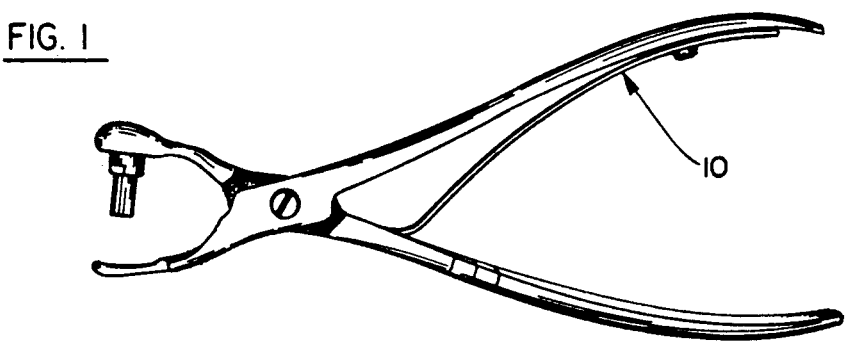
FIG. 1 is a side view of an interspinous punch which is used in the process of the invention.
Figure 2:
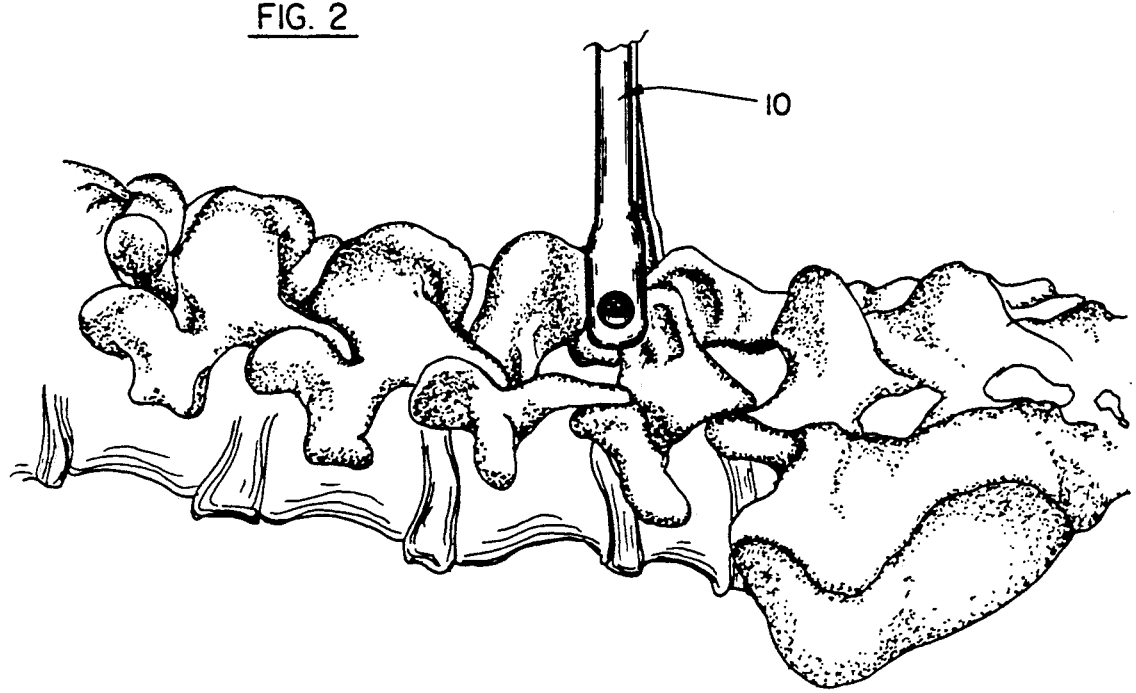
FIG. 2 shows the jaws of the punch position to punch a hole through the supraspinous ligament which covers the spine.

As explained above, the process of the invention involves, as a first step, punching a hole in the supraspinous ligament to provide a means for inserting a spreader between the lamina without necessitating the removal of the ligament. An appropriate interspinous punch is designated 10 in FIG. 1. FIG. 2 shows the punch in position to punch a hole in the supraspinous ligament (not shown) which normally covers the spinal column. Accordingly, the ligament is left intact, so that the spinal column is stabilized.

Figure 3:
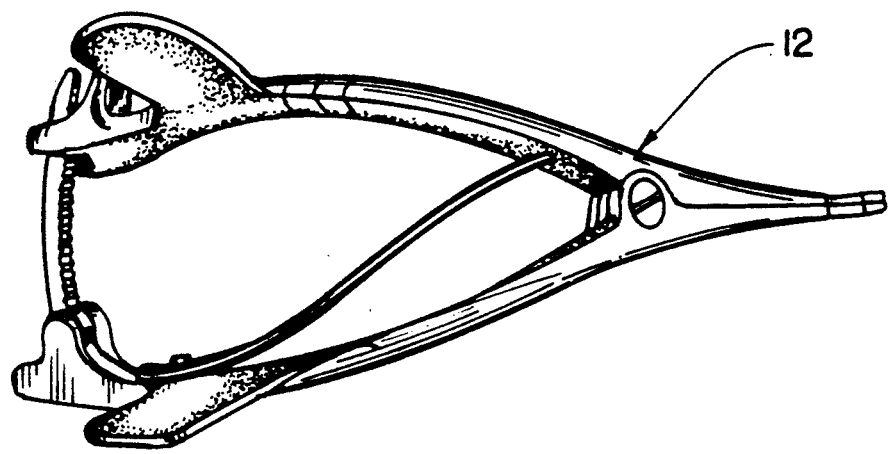
FIG. 3 is a top plan view of a lamina spreader instrument for use in the process of the invention.
Figure 4:
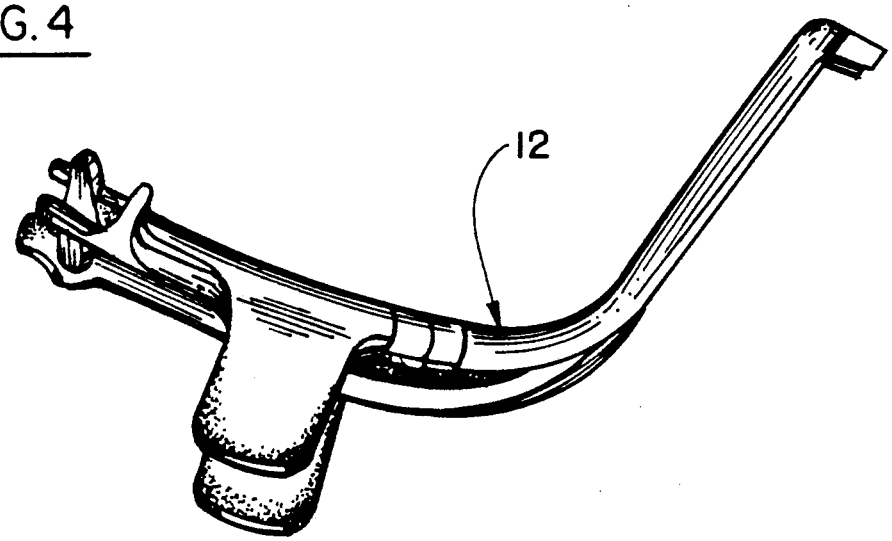
FIG. 4 is a side view of the instrument.

As a second step in the process, a lamina spreader 12 shown in FIGS. 2 and 3 is inserted through the hole made by the punch 10 in the ligament. As illustrated in FIGS. 3 and 4, the jaws of the spreader have an elongated narrow configuration, so that they may conveniently be inserted through the hole in the ligament in accordance with the second step of the process. Also, the curved configuration of the spreader keeps its handle out of the way of the microscope and surgeon during microscopic lumbar laminectomy surgical procedures.

Figure 5:
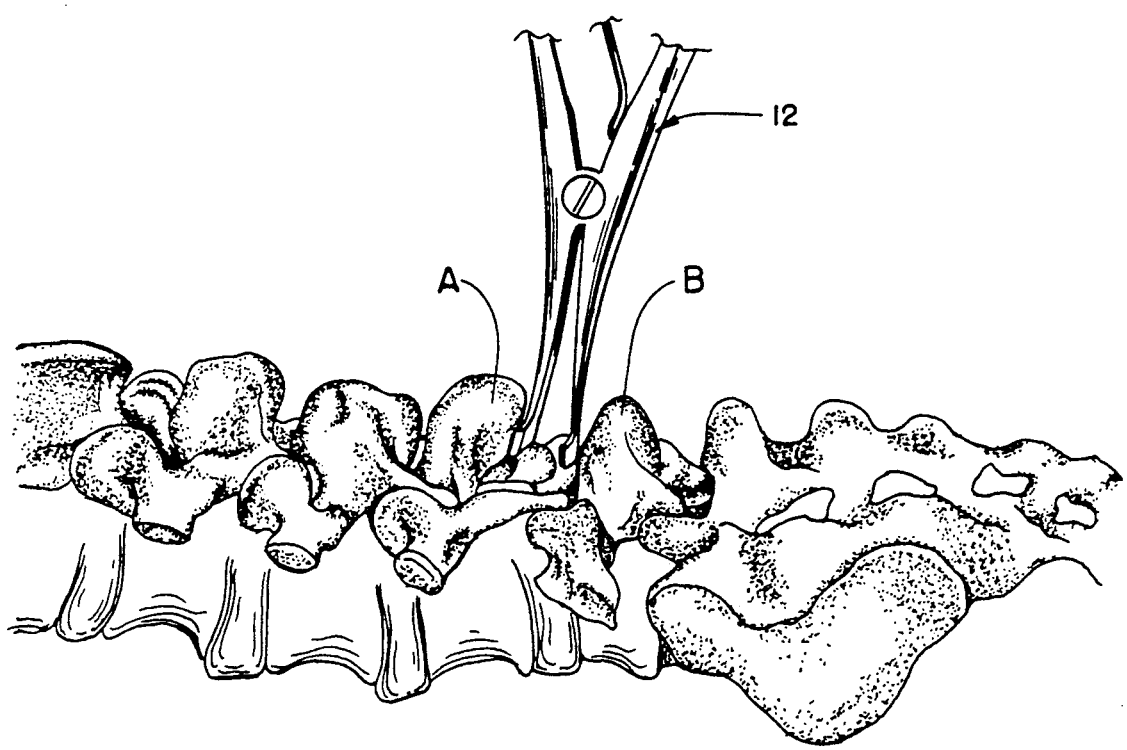
FIG. 5 shows the spreader being used to separate the lamina of the spinal column.

FIG. 5 shows the spreader 12 in position after it has been inserted through the hole in the ligament, and in the process of spreading lamina A and B of the spinal column to permit entrance by the surgeon into the interlaminal area with minimal bone removal for the performance of the surgical function.

It will be appreciated that while a particular embodiment of the process of the invention has been described above, and particular instruments for carrying out the process have been shown and described, modifications may be made. It is intended in the following claims to cover all modifications which come within the spirit and scope of the invention.

I claim:

1. A laminectomy surgical process which involves the entrance into the interlaminal area of the spine, and which comprises the following steps: (a) punching a hole in the ligament covering the lamina of the spine; and (b) inserting a lamina spreader instrument through the hole in the ligament to engage and spread the lamina so as to open up the space there-between with the ligament in place, and with the ligament preventing any tendency for the instrument to slip out of the wound.

2. The process defined in claim 1, in which the spreader has a curved configuration so as to prevent any interference with the positioning of a microscope during microscopic laminectomy or with the surgeon during the procedure.

* * * * *